United States Patent
Wallace et al.

(10) Patent No.: US 8,005,790 B2
(45) Date of Patent: Aug. 23, 2011

(54) OBJECT CLONING MANAGEMENT SYSTEM AND METHOD

(75) Inventors: William Eric Wallace, Waterloo (CA); Tatjana Tunguz, Waterloo (CA)

(73) Assignee: AGFA Healthcare N.V., Mortsel (BE)

( * ) Notice: Subject to any disclaimer, the term of this patent is extended or adjusted under 35 U.S.C. 154(b) by 274 days.

(21) Appl. No.: 11/703,129

(22) Filed: Feb. 7, 2007

(65) Prior Publication Data

US 2008/0189317 A1   Aug. 7, 2008

(51) Int. Cl.
G06F 17/30   (2006.01)
(52) U.S. Cl. .......................... 707/626; 707/756
(58) Field of Classification Search ............... 707/104.1, 707/204–205, 200, 10, 3; 713/200, 164; 709/219, 226; 365/185.17
See application file for complete search history.

(56) References Cited

U.S. PATENT DOCUMENTS

| | | | | |
|---|---|---|---|---|
| 5,129,088 A | * | 7/1992 | Auslander et al. | 711/1 |
| 5,566,331 A | * | 10/1996 | Irwin et al. | 707/10 |
| 5,758,360 A | * | 5/1998 | Zbikowski et al. | 707/205 |
| 5,907,837 A | * | 5/1999 | Ferrel et al. | 707/3 |
| 5,946,685 A | * | 8/1999 | Cramer et al. | 707/200 |
| 6,356,915 B1 | * | 3/2002 | Chtchetkine et al. | 707/200 |
| 7,131,000 B2 | * | 10/2006 | Bradee | 713/164 |
| 7,197,502 B2 | * | 3/2007 | Feinsmith | 1/1 |
| 2001/0047400 A1 | * | 11/2001 | Coates et al. | 709/219 |
| 2002/0133504 A1 | * | 9/2002 | Vlahos et al. | 707/104.1 |
| 2003/0145086 A1 | * | 7/2003 | O'Reilly | 709/226 |
| 2004/0024578 A1 | * | 2/2004 | Szymanski et al. | 703/17 |
| 2004/0034661 A1 | * | 2/2004 | Barron et al. | 707/104.1 |
| 2004/0236788 A1 | * | 11/2004 | Sato et al. | 707/104.1 |
| 2005/0097352 A1 | * | 5/2005 | Patrick et al. | 713/200 |
| 2007/0103984 A1 | * | 5/2007 | Kavuri et al. | 365/185.17 |

OTHER PUBLICATIONS

Chao Jin, Weimin Zheng, Feng Zhou, Yinghui Wu, "A Distributed Persistent Object Store for Scalable Service", 2002, www.cs.berkeley.edu/.*
Mesnier M et al: "Object-Based Storage", IEEE Communications Magazine, IEEE Service Center. Piscataway, N.J. US, vol. 41, No. 8. Aug. 2003.*

* cited by examiner

*Primary Examiner* — Sheree Brown
(74) *Attorney, Agent, or Firm* — Bereskin & Parr LLP; Isis E. Caulder (57) ABSTRACT

A system and method for automatically handling data objects within groupings in a PACS network. Where a data object belonging to one grouping is moved to or copied into another grouping, certain associated data objects will automatically be moved or copied to the other grouping. Similarly, where some data objects are deleted from a grouping, data objects associated with objects which will not be deleted are automatically protected from deletion.

11 Claims, 6 Drawing Sheets

OBJECT CLONING MANAGEMENT SYSTEM AND METHOD

FIELD

The embodiments described herein relate to a system and method for image storage and more particularly to a system and method for moving image data within an image storage system.

BACKGROUND

Medical imaging has been an expanding field for several decades. With increasing diagnostic tools, increasing population, more wide-spread access to medical treatment, and the desirability of sharing information between doctors and professionals, medical imaging is likely to continue growing at a rapid rate. To address this continued growth, and the subsequent inconveniences of paper and other fixed forms of medical image storage, the medical community has increasingly turned to digital forms of image storage.

Picture Archiving and Communications Systems (PACS) are a common example of a digital image system. Enterprise PACS deployments, such as those found in a hospital, provide a centralized means of searching, retrieving and storing images using the Digital Imaging and Communications in Medicine (DICOM) protocol.

According to the DICOM protocol, each digital image is stored as a DICOM object which includes the raw image data as well as associated meta-data such as the name of the patient of whom the image was taken and the date on which the image was captured. For each originally captured image there may be more than one associated DICOM image object.

Other DICOM objects contain information regarding the manner in which an image is to be displayed or clinical information which may be related to an image or images. These types of DICOM objects do not include raw image data but may include references to DICOM image objects which do include image data.

The DICOM objects stored in digital image systems such as PACS are often organized into groups, called studies. Each study normally includes the DICOM objects which relate to one particular patient for a particular purpose. One study may include many different types of DICOM objects, with various references connecting them.

For various reasons, DICOM objects from one study may need to be moved or copied to a different study, such as when a study is merged, split, or segmented. This is often done by creating a duplicate or "clone" of the original object in the target study and, if necessary, deleting the original object from the source study. Problems may arise, however, when a cloned object includes references to, or is referenced by, other objects in the source study. If these other objects are not cloned along with the object to which they relate, information may be lost. Similar problems may arise when deleting objects from the source study. If an object which references or is referenced by another object is deleted then that reference will be broken.

Previous solutions to these problems put the burden on the user to select which objects to clone and which objects to leave in the original study. This can be both time consuming and error prone as the user may not be aware of all the relationships between the objects and some objects, particularly those which do not include raw image data, may not be visible to the user. Another possible solution to this problem is to move the original object to the target study rather than cloning it, thus preserving references between the objects. However, this violates several standards and causes significant other problems. For instance, according to one DICOM standard, each time a change is made to a study, a new DICOM object needs to be generated. By moving the original objects to the target study rather than creating new objects, this DICOM standard is violated.

Thus, it would be desirable to have a method for automatically selecting data objects which are in some way associated with a set of cloned data objects to be similarly cloned while still protecting those objects which must remain in the source study from deletion. This would reduce the burden on the user to decipher the maze of references within a study and allow both the cloned objects and the original objects to function correctly with no loss of information.

SUMMARY

The invention provides in one aspect, a method of duplicating one or more data objects in an image storage network having one or more data objects categorized into a first category of objects and a second category of objects, the method comprising:
(a) selecting a base set of one or more data objects from the first category of objects;
(b) duplicating the base set;
(c) selecting one or more data objects from the second category of objects which are not included in the base set and which are associated with one or more objects in the base set;
(d) adding the data objects selected in (c) to the base set;
(e) duplicating the data objects selected in (c); and
(f) repeating (c) to (e) until no data objects are selected in (c).

In another aspect, the present invention provides a clone management system for duplicating one or more data objects in an image storage network having one or more data objects categorized into a first category of objects and a second category of objects, the system comprising:
(a) a memory for storing the one or more data objects;
(b) a processor coupled to the memory configured for:
(i) selecting a base set of one or more data objects from the first category of objects;
(ii) duplicating the base set;
(iii) selecting one or more data objects from the second category of objects which are not included in the base set and which are associated with one or more objects in the base set;
(iv) adding the data objects selected in (iii) to the base set;
(v) duplicating the data objects selected in (iii); and
(vi) repeating (iii) to (v) until no data objects are selected in (iii).

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The embodiments of the systems and methods described herein may be implemented in hardware or software, or a combination of both. However, preferably, these embodiments are implemented in computer programs executing on programmable computers each comprising at least one processor, a data storage system (including volatile and non-volatile memory and/or storage elements), at least one input device, and at least one output device. For example and without limitation, the programmable computers may be a personal computer, laptop, personal data assistant, and cellular telephone. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and pre-defined manner to perform the functions described herein.

Figure 1:
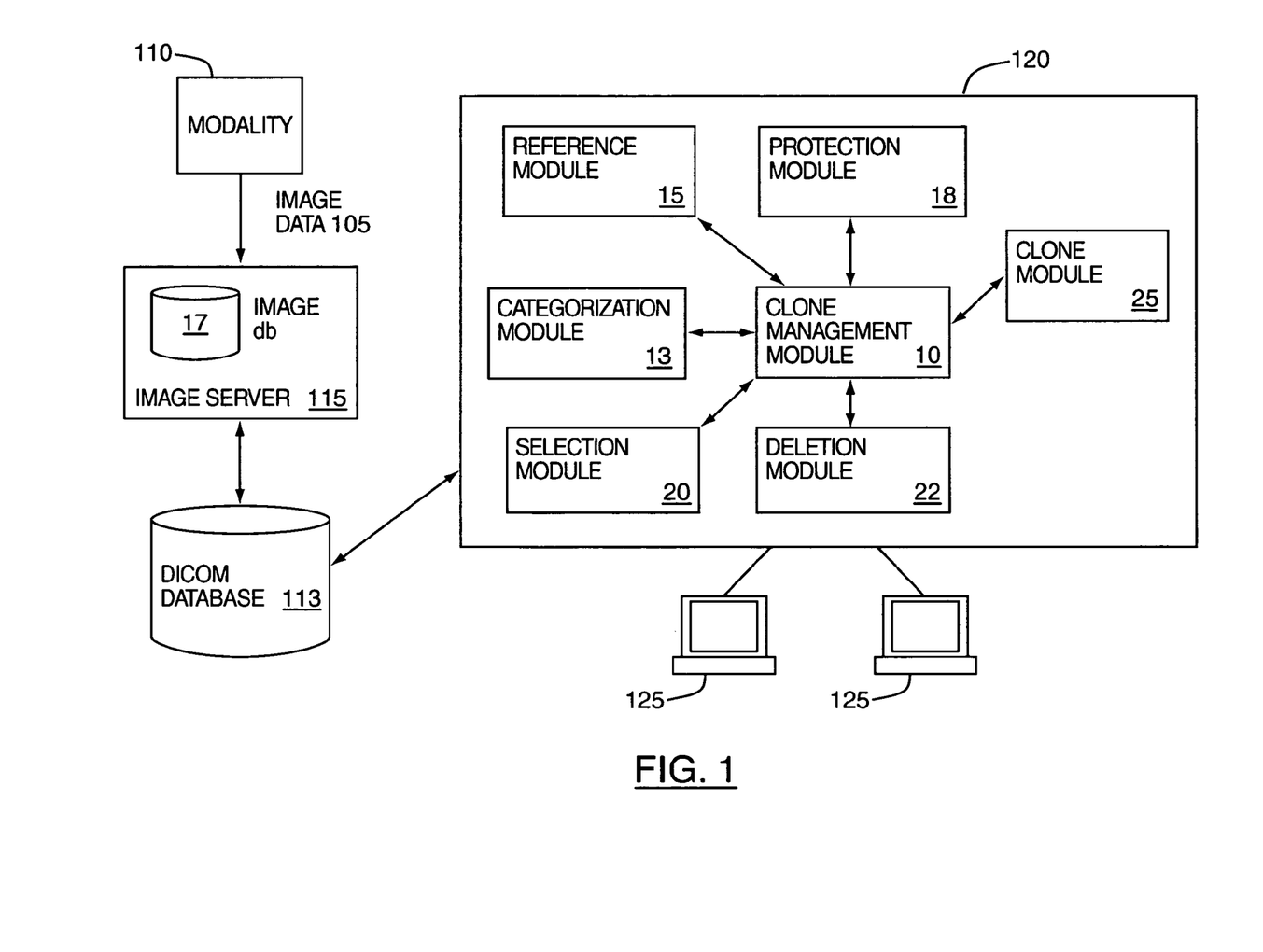
FIG. 1 is a block diagram of a clone management system.

Reference is first made to FIG. 1, which is a block diagram illustrating the basic components of a clone management system 120 which forms part of a PACS system. The clone management system 120 includes a clone management module 10, a categorization module 13, a reference module 15, a protection module 18, a selection module 20, a deletion module 22, and a cloning module 25. Image data 105 is acquired by imaging modality 110 and stored in an image database 17 on an image server 115. Image data is then transferred to a DICOM database 113, using a communication protocol, such as one of the DICOM communication protocols.

It should be understood that the clone management system 120 may be implemented in hardware or software or a combination of both. Specifically, the modules of the clone management system 120 are preferably implemented in computer programs executing on programmable computers each comprising at least one processor, a data storage system, and at least one input and at least one output device. Without limitation, the programmable computers may be a server, personal computer, laptop, personal data assistant or cellular telephone. In some embodiments, the clone management system 120 is installed on the hard drive of the user workstation 125 within a PACS system, such that the user workstation 125 operates with the PACS system in a client-server configuration. In other embodiments, the clone management system 120 can run from a single dedicated workstation that may be associated directly with a particular modality 110. In yet other embodiments, the clone management system 120 can be configured to run remotely on the user workstation 125 while communication with the PACS system occurs via a wide area network (WAN), such as through the internet.

Users of a PACS system may access the image data stored in the DICOM database 113 using a workstation 125, which may be a computer workstation consisting of a processor, display device and input devices (e.g., keyboard, mouse). Alternatively, the workstation 125 may be a mobile device or any other suitable access device for displaying image data.

Each image data file generated from the image data 105 can be expressed as two logical parts. One part is known as pixel data that represents the displayed image. The other logical part is the metadata that represents a set of attributes that describes the image such as patient information, study grouping, and image attributes.

For each originally captured image, there may be more than one associated image data file. For example, digital mammography images can be digitally processed such that, when displayed, the key features required for mammographic interpretation will be demonstrated. Separate image data files will be used to store the original and processed images. The DICOM Digital Mammography X-Ray Image Information (MG) object, for example, includes one of two types of image data: "For processing" image data which has not been processed for interpretation; or "For presentation" image data which has been processed and is ready to be displayed. Processed image data files such as these will normally include a reference identifying the image data file of the original image.

Other data files stored in the DICOM database 113 may include information relating to the way in which an image is to be presented. These data files will not include image data but will include a reference to the image data file(s) to which they are to be applied. For example, the DICOM grayscale presentation state (GSPS) object stores the viewing parameters for a DICOM image objects in order to allow for the consistent presentation of the images. A GSPS object may reference more than one image object and, conversely, there may be more than one GSPS object which references a single image object.

The structured reporting (SR) class of DICOM objects are used for transmission and storage of clinical documents. Again these objects do not contain image data but provide the capability to link text and other data to particular images. Computer-aided detection (CAD) SR objects, for example, include a reference to the image on which the detection was performed and allow the location of CAD findings to be displayed on the image.

The data files stored in the DICOM database 113 are often saved into groups, called studies. Each study includes the data files which relate to one particular patient for a particular purpose. One study may include many different types of data files, including image data files such as DICOM Computed Tomography (CT) and Magnetic Resonance Imaging (MR) objects as well as non-image data files such as DICOM GSPS and SR objects.

Clone management module 10 allows data files to be copied or transferred from one study to another study in the DICOM database 113 while maintaining consistency in references between data files. For example, operations such as the merge, split and segment operation all require the coping or transferring of data files. In each of these operations, a data file from a source study is duplicated or "cloned" in a target study using cloning module 25. The original data file may or may not be deleted from the source study using deletion module 22. It is important to note that when a data file is deleted using deletion module 22, it may still exist in a hidden form so that it appears to a user to have been completely removed from the system but it may still be retrieved if it is necessary to return the study to its original state.

Figure 2A:
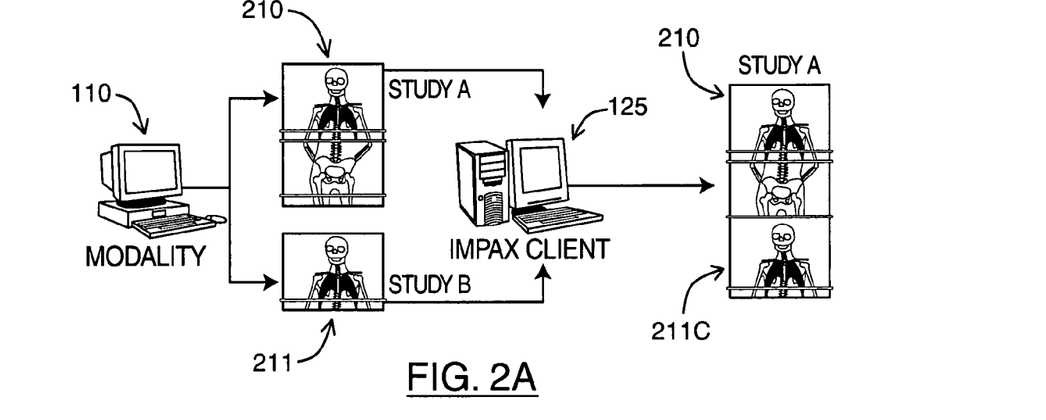
FIG. 2A is a flowchart diagram illustrating a merge operation.
Figure 2B:
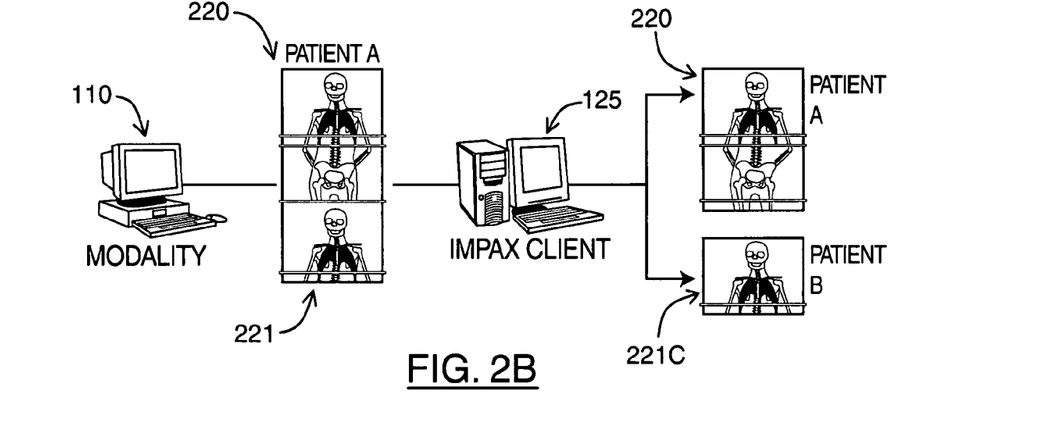
FIG. 2B is a flowchart diagram illustrating a split operation.
Figure 2C:
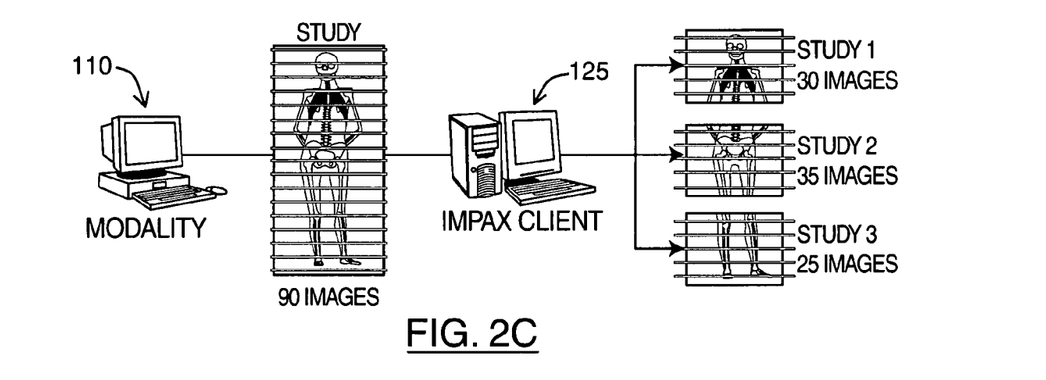
FIG. 2C is a flowchart diagram illustrating a segment operation.

FIGS. 2A to 2C show examples of the merge, split and segment operations that may be performed using the clone management system 120 in a PACS system. In these examples, the PACS being employed is an IMPAX system, with the workstation 125 functioning as an IMPAX client, but any PACS that supports the merge, split and segment operations could be substituted.

A merge operation is used when objects from two or more studies must be merged into a single study. For example, if a new study is accidentally started while data is being collected, a merge operation may be used to correct the error. Similarly, when images of two or more types are collected from a patient, the images will often start off in different studies. The merge operation may be used to consolidate all the data related to that patient in one study.

Referring now to FIG. 2A, there is shown a flowchart diagram of an example merge operation. Image data relating to two different images is received from the modality 110 and stored in two image data files, 210 and 211. Image data file 210 has been stored in Study A and image data file 211 has been stored in Study B. Studies A and B are then selected to be merged into Study A using the workstation 125. The objects in Study B are then cloned and the cloned objects are placed in Study A. All of the objects contained in Study B are then deleted. As a result Study A includes both image object 210 and image object 211c that is a clone of image object 211.

The split operation is used to create multiple studies from a single study. This is useful when images from one patient are mistakenly included in a study for another patient.

Referring now to FIG. 2B, there is shown a diagram of a possible split operation. Image data relating to two different images is received from the modality 110 and stored in two image data files, 220 and 221. Image data file 220 relates to patient A and image data file 221 relates to patient B but both objects have been mistakenly stored in a single study for patient A. Image data file 221 is then selected to be split from the study for patient A and included in a new study for patent B using the workstation 125. A new study for patient B is created including a clone of image data file 221. Image data file 221 is then deleted from the study for patent A. As a result, the study for patient A includes only image data file 220 and the study for patient B includes only image data file 221c, the clone of image data file 221.

A segment operation is used to break a single study into multiple studies for one patient. This could be required, for example, when a number of different specialists all need to view different objects which, for cost and convenience, have been stored as a single study. The segment operation may also be used to assign a data file to more than one study. For example, if three studies were scheduled but only one was performed, a segment operation could be used to copy images from the performed study to all of the scheduled studies.

Referring now to FIG. 2C, there is shown a diagram of a possible segment operation. Image data relating to ninety different images is received from the modality 110 and stored a single study. A segment operation is performed using the workstation 125. In this example, the first 30 objects are selected for Study 1, the next 35 objects are selected for Study 2 and the last 25 objects are selected for Study 3. Study 1 is created with clones of each of the first 30 objects, Study 2 is created with clones of each of the next 35 objects and Study 3 is created with clones of each of the last 25 objects. The original study is then deleted resulting in the three studies shown.

Figure 3A:
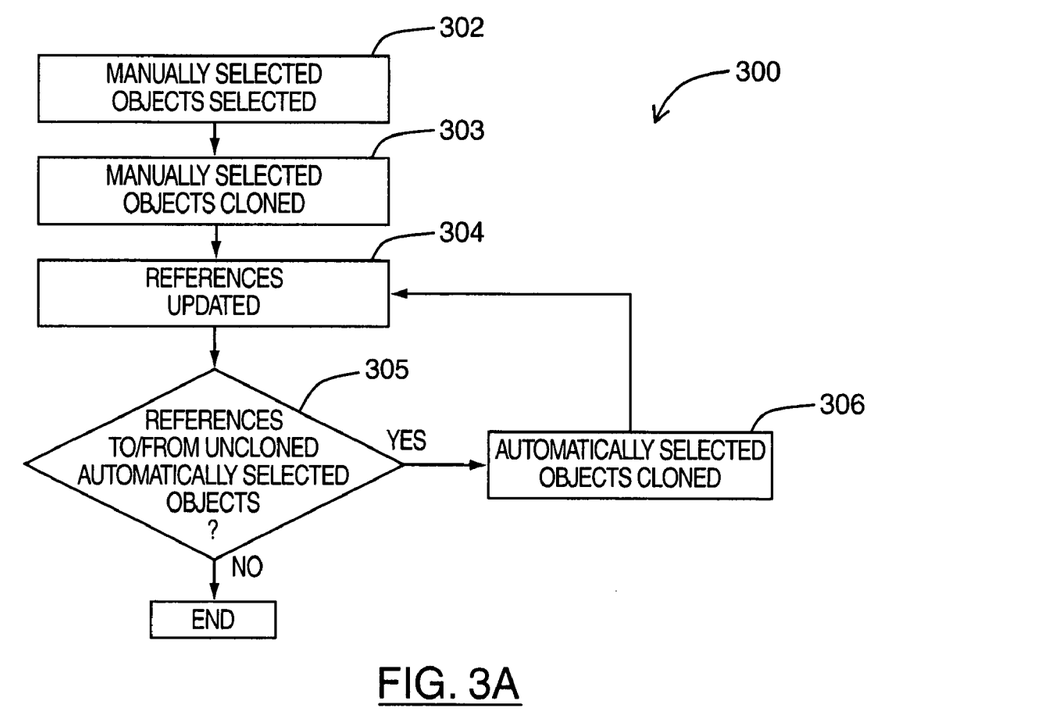
FIG. 3A is a flowchart diagram illustrating the steps required to automatically clone objects associated with a cloned object.

Referring now to FIG. 3A, there is shown a flowchart diagram that illustrates the method 300 used to process certain data files which reference cloned data files or which are referenced by cloned data files. In operations, such as split and segment operations, where some objects may be kept in the original study and other objects deleted from the original study, the method 300 will also ensure that certain types of data files which reference or are referenced by a data file which will remain in the original study will not be deleted from the original study.

For the purposes of the method 300, the data files in a study are divided into categories using categorization module 13. The first category consists of manually selected objects and includes all data files which must be selected by the user for cloning. These may include displayable objects such as DICOM MG For Presentation, CT and MR objects as well as some non-displayable objects such as waveform, stand-alone overlays and some SR objects. The second category consists of automatically selected objects including data files that will be handled automatically by the method 300. The user is not required to determine whether or not these objects should be cloned and/or deleted from a source study. This category will include objects which always reference manually selected objects such as DICOM GSPS objects, Colorscale Softcopy Presentation State (CSPS) objects, CAD SR objects and MG For Processing objects.

There may also be a third category of semi-automatically selected objects for which the image or study may need to be examined in order to determine if the object can be handled automatically. For example, SR objects which are not CAD SR objects, can, but do not always, contain references to manually selected objects. If they do contain such references, these objects may be placed in the automatically selected category. Otherwise, they will be placed in the manually selected category. The same is true for secondary capture objects such as overlays of measurements added into an original image. These objects must be categorized using categorization module 13 before they can be processed by clone management module 10.

At step (302), the user defines a base set by selecting all manually selected objects which they wish to move or copy to another location. If this were a merge operation, the base set would include all the objects in an original study which are selected to be merged into the target study. In a split operation, the base set would include those which are selected to be moved to the new target study. In a segment operation, the base set would include all the objects selected to be moved to a certain target study. The base set will include all the objects from the original study which have been cloned. A target set includes all the objects in the target study including the clones of objects in the base set. In the case of a merge operation, for example, the target set would initially include all the objects in the study into which objects will be merged. In a split or segment operation, the target set will initially be empty.

At step (303), the manually selected objects in the base set are cloned using cloning module 25 and the clones are placed in the target set. At step (304), references between cloned objects are updated using reference module 15 such that if an object which has been cloned references another object which has been cloned, then the clone of the first object will now reference the clone of the second object. This can be done either by adding a new reference to/from the cloned object or by replacing the old reference with a reference to/from the cloned object.

At step (305), the automatically selected objects in the original study which have not yet been cloned are checked to determine if they reference or are referenced by an object in the base set. If there are any such objects, these objects are selected to be included in the base set by selection module 20, cloned at step (306) using cloning module 25 and the clones are included in the target set. The references are then updated at step (304) by reference module 15. This process continues until there are no automatically selected objects in the original study which reference or are referenced by a cloned object and are not in the base set. If this were a segment operation, the method 300 may return to step (302) to complete the process for the next target study.

Figure 3B:
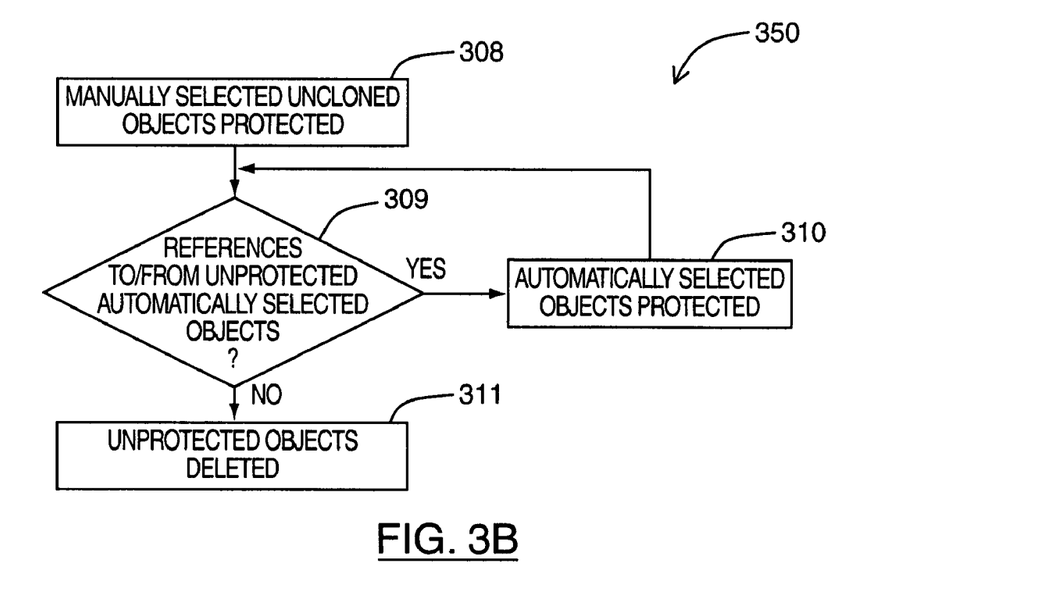
FIG. 3B is a flowchart diagram illustrating the steps required to automatically delete objects associated with a cloned object.

Referring now to FIG. 3B, there is shown a flowchart diagram that illustrates the method 350 used to handle the deletion certain data files which reference cloned data files or which are referenced by cloned data files. This method need only be employed if the type of operation being performed is a type of operation in which some, but not necessarily all, of the objects from the original study which have been cloned will be deleted from the original study. For example, in the case of a merge operation, the original studies which are not the target study will be entirely deleted. In this case the method 350 is unnecessary. However, in a split operation, only the manually selected objects which have been selected to be split are deleted from the original study. Those manually selected objects in the original study which are not selected will remain in the original study. In this case, the method 350 would be employed.

At step (308), all manually selected objects in the original study which are not part of the base set will be marked as "protected" by protection module 18 which means they will not be deleted from the original study. Next, at step (309), the automatically selected objects in the original study are checked to determine if any of them reference or are referenced by a protected object. If so, those objects are selected using selection module 20 and are also marked as protected at step (310) by protection module 18. This process continues until there are no unprotected automatically selected objects which reference or are referenced by a protected object. The method 300 then continues to step (311), where all unprotected objects are deleted from the original study using deletion module 22.

Figure 4:
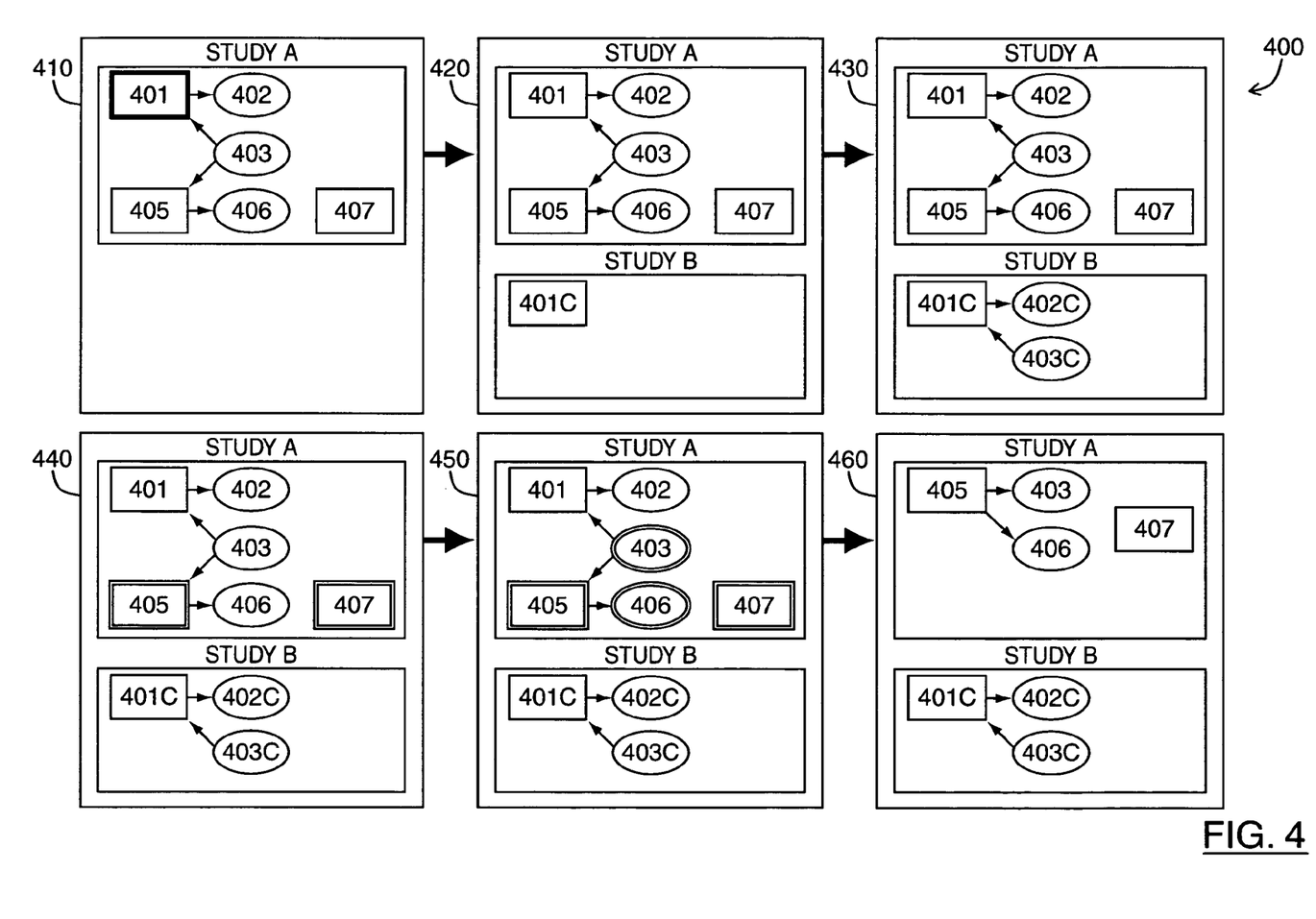
FIG. 4 is a dataflow diagram illustrating an example of a split operation.

Referring now to FIG. 4, there is shown a dataflow diagram that illustrates an example split operation 400 according to the method 300 and the method 350 discussed above.

As shown at 410 in this example, Study A contains three manually selected objects indicated by boxes (401, 405, and 407) and three automatically selected objects indicated by ovals (402, 403, and 406). Object 401 references object 402, object 403 references objects 401 and 405, and object 405 references object 406.

The method 300 then begins at step (302) where object 401 is selected to be split. At step (303), the selected object, object 401, is cloned. Study B now contains object 401c, the clone of object 401, as shown in 420. As there are no references to or from object 401 in Study B, the method 300 proceeds to step (305). At this point object 401c will contain a reference to 402 in the original study (not shown for clarity).

At step (305) it is determined that there are references from object 401 to object 402 and to 401 from object 403 and that both 402 and 403 have not been cloned. These objects are then cloned at step (306) and the references in Study B are updated at step (304) so that 401c refers to 402c and 403c refers to 401c. This is shown in 430. Step (305) then repeats. As there are no further references to automatically selected uncloned objects, the method 300 ends. Since this is a split operation, the method 350 will also be employed.

At step (308) of method 350 all the manually selected objects which were not cloned in step (303) of method 300 are marked as protected. This is indicated in 440 by a double outline around objects 405 and 407. At step (309) it is determined that object 405 references automatically selected object 406 and is referenced by automatically selected object 403 which have not been protected. Hence, objects 403 and 406 are also marked as protected at step (310) as shown in 450.

The method 350 then repeats step (309) and determines that there are no further unprotected automatically selected objects with references to or from protected objects. Finally, at step (311), all the objects in Study A which have not been marked as protected are deleted and the method 350 terminates. The final contents of Studies A and B are shown in 460.

Figure 5:
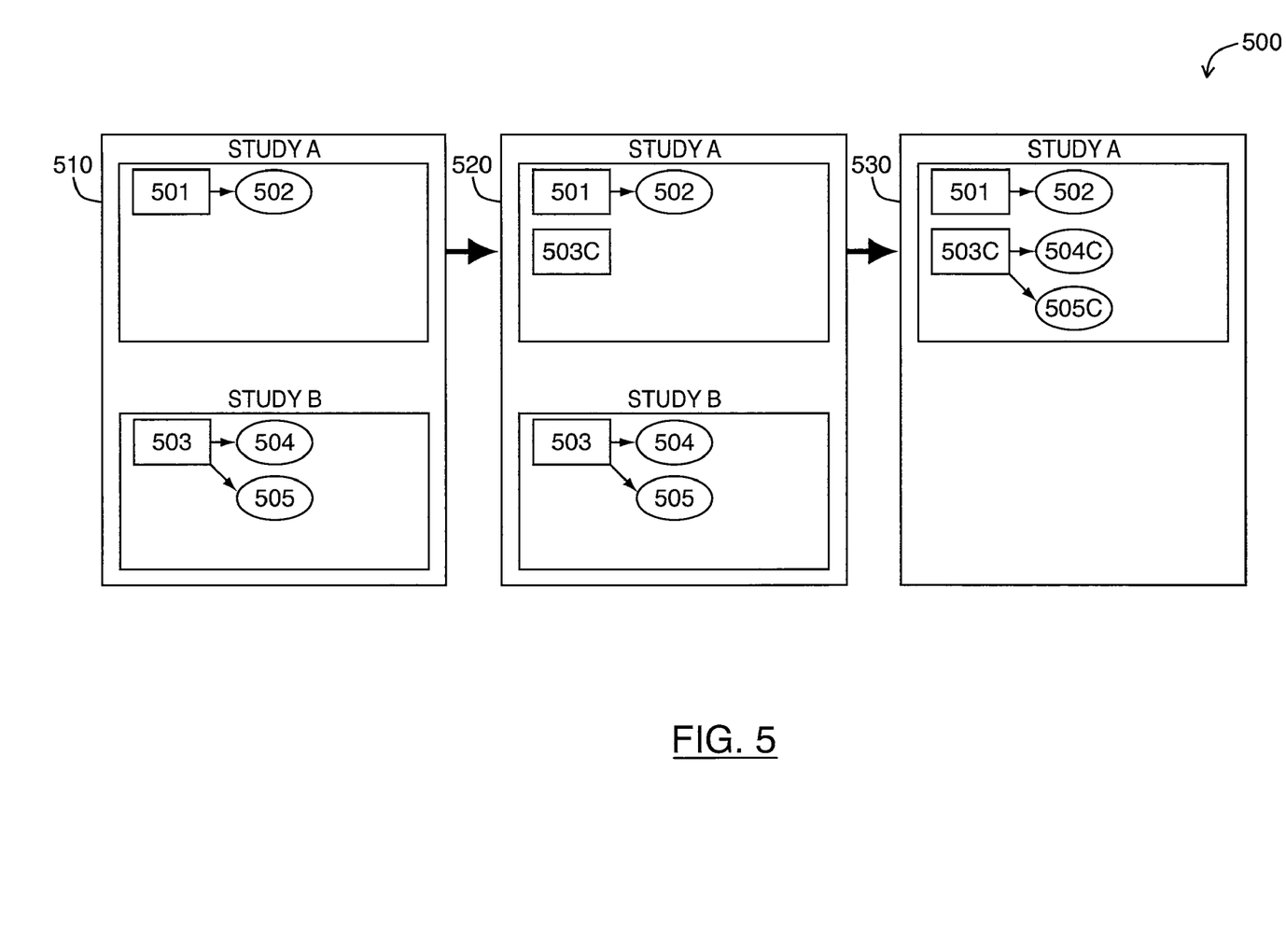
FIG. 5 is a dataflow diagram illustrating an example of a merge operation.

Referring now to FIG. 5, there is shown a dataflow diagram that illustrates an example merge operation 500 according to the method 300 and the method 350 discussed above. In this example, Study B is selected to be merged into Study A and hence, all the objects in Study B must be cloned into Study A.

As shown at 510 in this example, Study A contains one manually selected object indicated by a box (501) and one automatically selected object indicated by an oval (502). Object 501 references object 502. Study B contains one manually selected object (503) and two automatically selected objects (504 and 505). Object 503 references objects 504 and 505.

The method 300 then begins at step (302) where object 503 is selected to be cloned. At step (303), the selected object, object 503, is cloned. Study A now contains object 503c, the clone of object 503, as shown in 520. As there are no references to or from object 503 in Study A, the method 300 proceeds to step (305). At this point object 503c will contain a reference to objects 504 and 505 in the Study B (not shown for clarity).

At step (305) it is determined that there are references from object 503 to object 504 and to object 505 and that both 504 and 505 have not been cloned. These objects are then cloned at step (306) and the references in Study A are updated at step (304) so that 503c refers to 504c and 505c. This is shown in 530. Step (305) then repeats. As there are no further references to automatically selected uncloned objects, the method 300 ends. Since this is a merge operation, all existing object in Study B are deleted. There is no need to employ the method 350.

Figure 6:
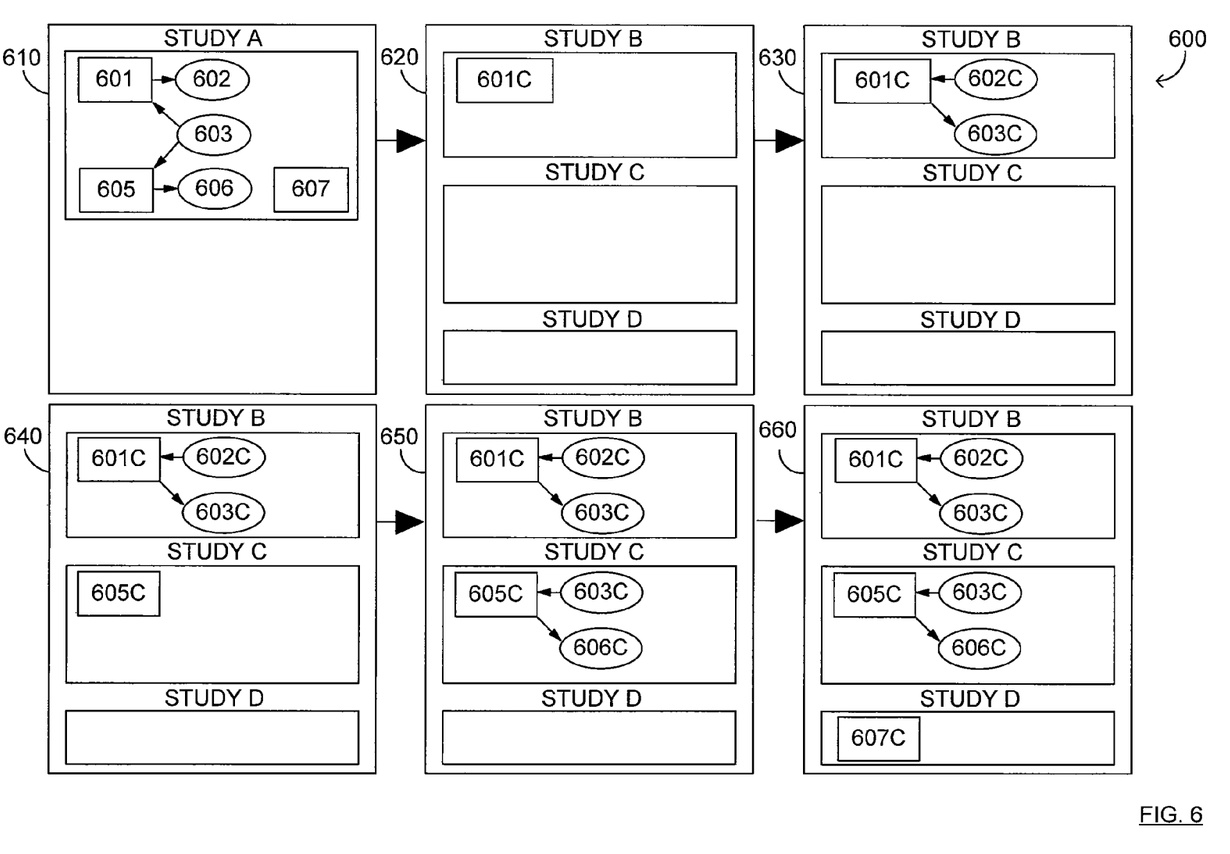
FIG. 6 is a dataflow diagram illustrating an example of a segment operation.

Referring now to FIG. 6, there is shown a dataflow diagram that illustrates an example segment operation 600 according to the method 300 and the method 350 discussed above. In this example Study A is to be segmented into three new studies: Study B, Study C and Study D.

As shown at 610 in this example, Study A contains three manually selected objects indicated by boxes (601, 605, and 607) and three automatically selected objects indicated by ovals (602, 603, and 606). Object 601 references object 602, object 603 references objects 601 and 605, and object 605 references object 606. Study B will be processed first.

The method 300 then begins at step (302) where object 601 is selected to be segmented into Study B. At step (303), the selected object, object 601, is cloned. Study B now contains object 601c, the clone of object 601, as shown in 620. As there are no references to or from object 601 in Study B, the method 300 proceeds to step (305). At this point object 601c will contain a reference to 602 in the original study (not shown for clarity).

At step (305) it is determined that there are references from object 601 to object 602 and to 601 from object 603 and that both 602 and 603 have not been cloned into Study B. These objects are then cloned at step (306) and the references in Study B are updated at step (304) so that 601c refers to 602c and 603c refers to 601c. This is shown in 630. Step (305) then repeats. As there are no further references to automatically selected uncloned objects, the method 300 ends. In this example, the method 300 must then be repeated for Study C.

The method 300 then begins again at step (302) where object 605 is selected to be segmented into Study C. At step (303), the selected object, object 605, is cloned. Study C now contains object 605c, the clone of object 605, as shown in 640. As there are no references to or from object 605 in Study C, the method 300 proceeds to step (305). At this point object 605c will contain a reference to 606 in Study A (not shown for clarity).

At step (305) it is determined that there are references from object 605 to object 606 and to 605 from object 603 and that both 606 and 603 have not been cloned into Study C. These objects are then cloned at step (306) and the references in Study C are updated at step (304) so that 605c refers to 606c and 603c refers to 605c. This is shown in 650. Step (305) then repeats. As there are no further references to automatically selected uncloned objects, the method 300 ends. The method 300 must then be repeated for Study D.

Again, the method 300 then begins at step (302) where object 607 is selected to be segmented into Study D. At step (303), the selected object, object 607, is cloned. Study D now contains object 607c, the clone of object 607, as shown in 660. As there are no references to or from object 607 in Study D, the method 300 proceeds to step (305).

At step (305) it is determined that there are no references to or from automatically selected uncloned objects and the method 300 ends. In this example, Study A may or may not be deleted but either way, there is no need to employ the method 350.

It will be appreciated that while reference has been made to storage and organization of medical imaging studies, the same system and method may be used for other data objects which may be managed in a PACS system. Furthermore, the system and method are not limited to the merge, split and segment operations and may be employed by any operation which requires data objects to be cloned.

It will further be appreciated that while PACS networks have been described in the context of medical image management in order to provide an application-specific illustration, it should be understood that PACS networks could also be applied to any other type of image or document display system. The system, processes and methods described are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A clone management system for duplicating one or more data objects of a plurality of data objects, the plurality of data objects being stored as a first study in a DICOM database, the system comprising:
    (a) a memory for storing the plurality of data objects;
    (b) a processor coupled to the memory configured for:
        (i) categorizing the plurality of data objects into a first category of manually selectable data objects and a second category of automatically selectable data objects;
        (ii) receiving input defining an initial base set of manually selected data objects, wherein the initial base set of data objects comprises one or more data objects from the first category of manually selectable data objects;
        (iii) duplicating the data objects in the initial base set, the duplicated initial base set being stored in a target study;
        (iv) determining one or more automatically selected associated data objects from the second category of automatically selectable data objects, wherein the one or more associated data objects from the second category:
            are not included in the duplicated initial base set, and
            either reference the one or more data objects in the initial base set or are referenced by the one or more data objects in the initial base set;
        (v) duplicating the one or more automatically selected associated data objects from the second category; and
        (vi) storing the duplicated one or more automatically selected associated data objects from the second category in the target study.

2. The system of claim 1, wherein (iii) and (vi) include updating references between data objects in the target study by:
    (A) selecting a data object in the target study having a reference to a data object from the first category of manually selectable data objects or the second category of automatically selectable data objects, the data object from the first category of manually selectable data objects or the second category of automatically selectable data objects having a duplicate in the target study;

(B) finding the duplicate of the data object from the first category of manually selectable data objects or the second category of automatically selectable data objects in the target study; and
(C) adding a reference from the selected data object in the target study to the duplicate of the data object in the target study.

3. The system of claim 1, wherein (iii) and (vi) include updating references between data objects in the target study by:
(A) selecting a data object in the target study having a reference to a data object from the first category of manually selectable data objects or the second category of automatically selectable data objects, the data object from the first category of manually selectable data objects or the second category of automatically selectable data objects having a duplicate in the target study;
(B) finding the duplicate of the data object from the first category of manually selectable data objects or the second category of automatically selectable data objects in the target study; and
(C) replacing the reference from the selected data object in the target study with a reference to the duplicate of the data object in the target study.

4. The system of claim 1, wherein said categorizing comprises placing data objects from a third category of data objects into the first category of manually selectable data objects or the second category of automatically selectable data objects, the third category of data objects comprising at least one semi-automatically selectable data object that needs to be examined to determine if the object can be handled automatically.

5. The system of claim 1, wherein the processor is further configured for:
(vii) marking a protected set of one or more data objects including data objects from the first category of manually selectable data objects which were not selected in (ii);
(viii) identifying one or more data objects from the second category of automatically selectable data objects which are not included in the protected set and are associated with one or more objects in the protected set;
(ix) adding the data objects identified in (viii) to the protected set;
(x) repeating (viii) to (ix) until no objects are identified in (viii); and
(xi) deleting objects from the plurality of data objects stored in the first study which are not in the protected set.

6. The system of claim 1, wherein the plurality of data objects stored in the first study is to be merged with at least one data object stored in the target study, the data objects selected in (ii) including all the data objects from the first category of manually selectable data objects selected to be merged with the at least one data object in the target study.

7. The system of claim 1, wherein a at least one of the plurality of data objects stored in the first study has been selected to be split from the first study, wherein the data objects selected in (ii) include all the objects from the first category of manually selectable data objects selected to be split from the first study and the target study is initially empty.

8. The system of claim 1, wherein the plurality of data objects stored in the first study has been selected to be segmented into two or more studies and wherein (ii) to (vi) are repeated once for each of the two or more segmented studies and the data objects selected in (ii) in each iteration include all the objects from the first category of manually selectable data objects in the first study which have been selected to be segmented into the current segmented set and the target study defined in (ii) in each iteration is the current segmented study.

9. The system of claim 1, wherein the system operates in an image storage network, the image storage network being a PACS network.

10. The system of claim 1, wherein at least one data object in the first category of manually selectable data objects is selected from the group consisting of: DICOM MG For Presentation objects, DICOM CT objects, DICOM MR objects, waveform objects, stand-alone overlay objects, and DICOM SR objects.

11. The system of claim 1, wherein at least one data object in the second category of automatically selectable data objects is selected from the group consisting of: DICOM GSPS objects, DICOM CSPS objects, CAD SR objects and MG For Processing objects.

* * * * *